US009174909B2

(12) United States Patent
Runge

(10) Patent No.: US 9,174,909 B2
(45) Date of Patent: Nov. 3, 2015

(54) TWO-STAGE, ACID-CATALYZED CONVERSION OF CARBOHYDRATES INTO LEVULINIC ACID

(75) Inventor: Troy Runge, Waunakee, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 870 days.

(21) Appl. No.: 13/364,472

(22) Filed: Feb. 2, 2012

(65) Prior Publication Data

US 2013/0204039 A1 Aug. 8, 2013

(51) Int. Cl.
B01J 31/04 (2006.01)
C07C 51/31 (2006.01)
C07C 59/185 (2006.01)
C07C 51/00 (2006.01)

(52) U.S. Cl.
CPC .................................... C07C 51/00 (2013.01)

(58) Field of Classification Search
None
See application file for complete search history.

(56) References Cited

U.S. PATENT DOCUMENTS

| 4,236,021 | A | | 11/1980 | Hsu et al. | |
|---|---|---|---|---|---|
| 4,897,497 | A | * | 1/1990 | Fitzpatrick | 549/489 |
| 4,916,242 | A | | 4/1990 | Avignon et al. | |
| 4,971,657 | A | | 11/1990 | Avignon et al. | |
| 5,608,105 | A | * | 3/1997 | Fitzpatrick | 562/515 |
| 5,892,107 | A | * | 4/1999 | Farone et al. | 562/515 |
| 6,054,611 | A | * | 4/2000 | Farone et al. | 562/515 |
| 6,642,396 | B1 | | 11/2003 | Zeitsch et al. | |
| 6,743,928 | B1 | | 6/2004 | Zeitsch et al. | |
| 6,955,743 | B2 | | 10/2005 | Rousu et al. | |
| 7,265,239 | B2 | | 9/2007 | Van De Graaf et al. | |
| 7,317,116 | B2 | * | 1/2008 | Sanborn | 549/483 |
| 7,520,905 | B1 | * | 4/2009 | Lightner | 44/388 |
| 7,579,489 | B2 | * | 8/2009 | Sanborn | 549/488 |
| 8,058,458 | B2 | * | 11/2011 | Sanborn | 549/488 |
| 8,399,688 | B2 | * | 3/2013 | Dumesic et al. | 549/326 |

FOREIGN PATENT DOCUMENTS

JP 62252742 A 11/1987

OTHER PUBLICATIONS

I.Agirrezabal-Telleria Applied Catalysis B: Environmental 115-116 (2012), pp. 169-178.*
Zhang et al. Industrial & Engineering Chemistry Research, 51 (2012), pp. 133-139.*
Efremov et al. International Symposium on Wood and Pulping Chemistry, 8th, Helsinki, Jun. 6-9, vol. 1 (1995), pp. 689-696.*
Antal, M. J.; Leesomboon, T.; Mok, W. S.; Richards, G. N., Mechanism of formation of 2-furaldehyde from D-xylose. *Carbohydrate Research* 1991, 217, 71-85.

Bond, Jesse Q. et al.; Integrated Catalytic conversion of γ-Valerolactone to Liquid Alkenes for Transportation Fuels, *Science* 2010, 327, 1110, DOI: 10.1126/science. 1184362.
Bozell, J., Production of levulinic acid and use as a platform chemical for derived products. *Resources, Conservation and Recycling* 2000, 28, (3-4), 227-239.
Cha, J.; Hanna, M., Levulinic acid production based on extrusion and pressurized batch reaction. *Industrial Crops and Products* 2002, 16, (2), 109-118.
Chang, C.; Cen, P.; Ma, X., Levulinic acid production from wheat straw. *Bioresource technology* 2007, 98, (7), 1448-1453.
Dias, A. S.; Pillinger, M.; Valente, A. A., Dehydration of xylose into furfural over micro-mesoporous sulfonic acid catalysts. *Journal of Catalysis* 2005, 229, (2), 414-423.
Dias, A. S.; Lima, S.; Carriazo, D.; Rives, V.; Pillinger, M.; Valente, A. A., Exfoliated titanate, niobate and titanoniobate nanosheets as solid acid catalysts for the liquid-phase dehydration of D-xylose into furfural. *Journal of Catalysis* 2006, 244, (2), 230-237.
Efremov, A. A.; Pervyshina, G. G.; Kuznetsov, B. N., Production of levulinic acid from wood raw material in the presence of sulfuric acid and its salts. *Chemistry of Natural Compounds* 1998, 34, (2), 182-185.
Edwards III, W. Preparation of oxycarboxylic acids. 4612391, 1986.
Fang, Q.; Hanna, M. A., Experimental studies for levulinic acid production from whole kernel grain sorghum. *Bioresource technology* 2002, 81, (3), 187-192.
Farnleitner, L.; Stueckler, H.; Kaiser, H.; Kloimstein, E. Preparation of stable levulinic acid. 3920340, 1991.
Fitzpatrick, S., Production of levulinic acid by the hydrolysis of carbohydrate-containing materials. *World Patent* 1997, 9640609.
Girisuta, B.; Janssen, L. P. B. M.; Heeres, H. J., Green Chemicals: A Kinetic Study on the Conversion of Glucose to Levulinic Acid. *Chemical Engineering Research and Design* 2006, 84, (5), 339-349.
Girisuta, B.; Janssen, L. P. B. M.; Heeres, H. J., Kinetic Study on the Acid-Catalyzed Hydrolysis of Cellulose to Levulinic Acid. *Industrial & Engineering Chemistry Research* 2007, 46, (6), 1696-1708.
Hayes, D. J.; Ross, P. J.; Hayes, P. M. H. B.; Fitzpatrick, P. S., The Biofine Process : Production of Levulinic Acid , Furfural and Formic Acid from Lignocellulosic Feedstocks. In 1999.
Leonard, R., Levulinic acid as a basic chemical raw material. *Industrial & Engineering Chemistry* 1956, 48, (8), 1330-1341.
Lima, S.; Pillinger, M.; Valente, A., Dehydration of d-xylose into furfural catalysed by solid acids derived from the layered zeolite Nu-6(1). *Catalysis Communications* 2008, 9, (11-12), 2144-2148.

(Continued)

*Primary Examiner* — Nyeemah A Grazier
(74) *Attorney, Agent, or Firm* — Joseph T. Leone, Esq.; DeWitt Ross & Stevens S.C.

(57) ABSTRACT

A method of producing levulinic acid from biomass is described. The method includes two acid treatment steps: first, treating biomass with a first aqueous acidic solution at a pH, for a time, and temperature such that at least a portion of pentosans contained within the biomass is extracted from the biomass, to yield pentosan-extracted biomass; second, treating the pentosan-extracted biomass with a second aqueous acidic solution at a pH, for a time, and a temperature, such that at least a portion of hexosans contained within the pentosan-extracted biomass are converted to levulinic acid.

19 Claims, 4 Drawing Sheets

(56) References Cited

OTHER PUBLICATIONS

Lourvanij, K.; Rorrer, G., Dehydration of glucose to organic acids in microporous pillared clay catalysts. *Applied Catalysis A: General* 1994, 109, (1), 147-165.

Montané, D., High-temperature dilute-acid hydrolysis of olive stones for furfural production. *Biomass and Bioenergy* 2002, 22, (4), 295-304.

Mosier, N.; Ladisch, C.; Ladisch, M., Characterization of acid catalytic domains for cellulose hydrolysis and glucose degradation. *Biotechnology and bioengineering* 2002, 79, (6), 610-618.

Tarabanko, V.; Chernyak, M.; Aralova, S.; Kuznetsov, B., Kinetics of levulinic acid formation from carbohydrates at moderate temperatures. *Reaction Kinetics and Catalysis Letters* 2002, 75, (1), 117-126.

Wiselogel, A.; Tyson, S.; Johnson, D., Biomass feedstock resources and composition. In *Handbook on Bioethanol: Production and utilization*, 1996; pp. 105-118.

\* cited by examiner

TWO-STAGE, ACID-CATALYZED CONVERSION OF CARBOHYDRATES INTO LEVULINIC ACID

FEDERAL FUNDING STATEMENT

This invention was made with government support under W911NF-08-02-0029 awarded by the ARMY/ARO. The government has certain rights in the invention.

BACKGROUND

An increase in crude oil prices and in the last decade, coupled with ongoing concerns regarding sustainability, have greatly increased interest in producing chemicals and fuels from renewable sources. Much current industrial focus has fallen on biomass to replace petroleum feedstocks. Lignocellulosic biomass is perhaps the most promising renewable feedstock because it offers the potential to provide sustainable sugar streams from a variety of high-volume materials including agricultural and forest residuals, and high-yielding bioenergy crops such as switchgrass, miscanthus, and hybrid poplar. One attractive option for the conversion of lignocellulosic biomass into renewable fuel and chemical production is the production of levulinic acid (LA) which is a very versatile platform chemical and widely used in the cosmetic, food, and medicinal industries'.

A number of approaches have been reported for LA synthesis, including hydrolysis of acetyl succinate esters[2], by acid hydrolysis of furfuryl alcohol[3], and by oxidation of ketones with ozone.[4] However, these methods frequently form large amounts of side products and intractable materials, or require an expensive feedstock. The most widely used approach is the dehydration of biomass or carbohydrates with acid.[5-12]

Furfural is another by-product of biomass that undergoes acid dehydration. Furfural is formed by the reactions of pentose sugars in the biomass, such as xylose. There currently is a market for furfural and its derivatives, including furfuryl alcohol which is used a binder for foundry forms. The chemistry of the furfural production involves the acid-catalyzed hydrolysis of the hemicellulosic pentose fractions of biomass and consecutive cyclodehydration of the pentose monomers, with xylose being the most predominant pentose in most biomass. Conventional mineral acids, such as sulfuric acid, are generally used as the catalysts.[13, 14] Within the past few years, several solid catalysts have also been introduced to catalyze xylose to furfural at a yield comparable to $H_2SO_4$.[15-17]

The theoretical yield of LA from C6-sugars is 100 mol %, or 64.5 wt % due to the co-production of formic acid.[18] In practice, using conventional methods, actual yield of LA from biomass rarely exceeds about 66% of the theoretical value (and is often much less). These lower yields are due to the formation of undesired black insoluble-materials called humins. The harsh acidic dehydration conditions utilized to hydrolyze and dehydrate hexoses to form LA from hexoses also hydrolyzes and dehydrates pentoses in the biomass to furfural, as shown in FIG. 1. In conventional approaches, the conditions are harsh enough that the furfural will further degrade and react with soluble saccharides forming solid humins. This loss of material both potentially lowers the LA yield as well as eliminates a value-added stream of furfural.

Thus, there remains a long-felt and unmet need to maximize the production of LA from biomass by minimizing the production of unwanted by-products such as humins.

SUMMARY OF THE INVENTION

At the heart of the present method is a two-stage, acid-catalyzed conversion of carbohydrates from biomass into levulinic acid (LA), a renewable platform chemical which can be used for fuels and chemicals. In the first step of the method, at least a portion of the pentoses (and preferably a majority of the pentoses) present in the biomass feedstock are removed. Removing at least a portion of the pentoses improves the LA yield by reducing the amount (and/or concentration) of furfural in the reaction mixture. This, in turn, reduces the amount of humins formed via from pentose degradation during the harsh acid conditions utilized during LA production. Thus, in the first step of the process, at least a portion of the pentoses in the biomass feedstock are removed, yielding a pentose-reduced biomass fraction. The pentose-reduced biomass fraction is then treated with acid (optionally in the presence of one or more catalysts) to yield LA.

In the preferred method, the two-stage conversion process starts with a mild acid extraction to remove the majority of the pentoses, while simultaneously maintaining the hexose sugars in solid form. Then the extracted solids (the pentose-reduced biomass fraction) are subjected to harsh conditions to produce LA with varying temperature, time, acid concentration, and a liquor-to-biomass ratio. These conditions were modeled and optimized with the best results obtained at high acid concentration, high temperature and low substrate consistency. A maximum molar yield of about 66% based on the hexose content, or 17.5 wt % based on the reactant biomass, was obtained under optimized conditions utilizing the two-stage process. A comparison of the two-stage process described herein to a one-stage acid process without the pentose extraction was performed, which indicated a marked molar yield decrease in LA yield to 49%, thus illustrating the utility of the method to increase LA yield.

The disclosure is thus directed to a method of producing levulinic acid from biomass. The method comprises treating biomass with an aqueous acidic solution at a pre-determined first pH, for a time, and at a temperature such that at least a portion of pentosans contained within the biomass is extracted from the biomass, to yield pentosan-extracted biomass. The pentosan-extracted biomass is then treated with an aqueous acidic solution at a pre-determined second pH (preferably lower than the first pH), for a time, and at a temperature, such that at least a portion of hexosans contained within the pentosan-extracted biomass are converted to levulinic acid.

The pH, time, and temperature of the acid treatments preferably are selected such that in the first step, the amount of pentosans extracted from the biomass is maximized, while the extraction of hexosans from the biomass is minimized. To increase contact of the biomass with the extraction solution, it is preferred that the biomass be comminuted in some fashion, as by chipping, grinding, and the like.

Preferably, the first step (to extract the pentosans from the biomass) comprises treating the biomass with an aqueous acidic solution having a pH of from about 0.8 to about 1.5, more preferably from about 0.9 to about 1.2, and most preferably from about pH 0.8 to about pH 1.0. The treatment temperature preferably ranges from about 100° C. to about 300° C., more preferably from about 125° C. to about 200° C., and more preferably still from about 125 to 175° C. The treatment duration preferably ranges from about 5 minutes to about 5 hours, more preferably from about 10 minutes to about 3 hours, and more preferably still from about 10 minutes to about 1 hour.

The second acid treatment step, in which the now pentosan-extracted biomass solids are treated with a second acid solution, it is preferred that the second pH be lower (i.e., more acidic) that than the first treatment step. Thus, in the second step, it is preferred that the aqueous acidic solution has a pH of from about 0.2 to about 0.6, more preferably about 0.2 to 0.4. The temperature of the second acid treatment step is preferably from about 100° C. to about 300° C., more preferably from about 150° C. to about 250° C., and more preferably still from about 170° C. to about 190° C. In the same fashion as the first treatment step, the second step preferably has a duration ranging from about 5 minutes to about 5 hours, more preferably from about 10 minutes to about 3 hours, and more preferably still from about 10 minutes to about 1 hour.

Times, temperatures, and pH's outside of the ranges noted above are within the scope of the method.

Any acid, now know or developed in the future, may be used in the aqueous acidic solutions. It is preferred that the aqueous acidic solution comprises a mineral acid or a Lewis acid. If a mineral acid is used, it is preferred that it is selected from the group consisting of hydrochloric acid, nitric acid, phosphoric acid, sulfuric acid, boric acid, hydrofluoric acid, and hydrobromic acid. Sulfuric acid is the preferred mineral acid.

The method may also further comprise separating the first aqueous acidic solution from the pentosan-extracted biomass. This first acidic solution is rich in extracted pentosans. The pentosans contained in the first aqueous acidic solution may be converted into furfural by any means known in the art or developed in the future. See, for example, U.S. Pat. Nos. 6,955,743; 6,743,928; 6,642,396; 4,916,242; and 4,971,657, which are incorporated herein by reference.

DETAILED DESCRIPTION

Figure 1:
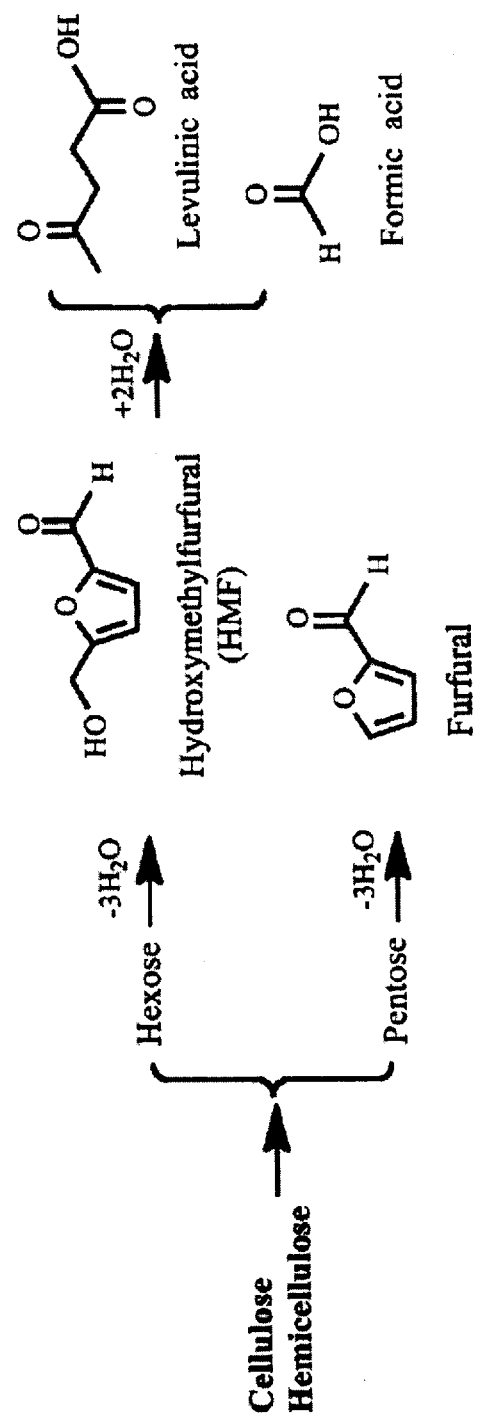
FIG. 1 is reaction pathway depicting the hydrolysis and degradation of cellulose and hemicelluloses. As shown in the figure, hexoses pass through an HMF intermediate to levulinic acid. Pentoses pass through a furfural intermediate to formic acid.
Figure 2:
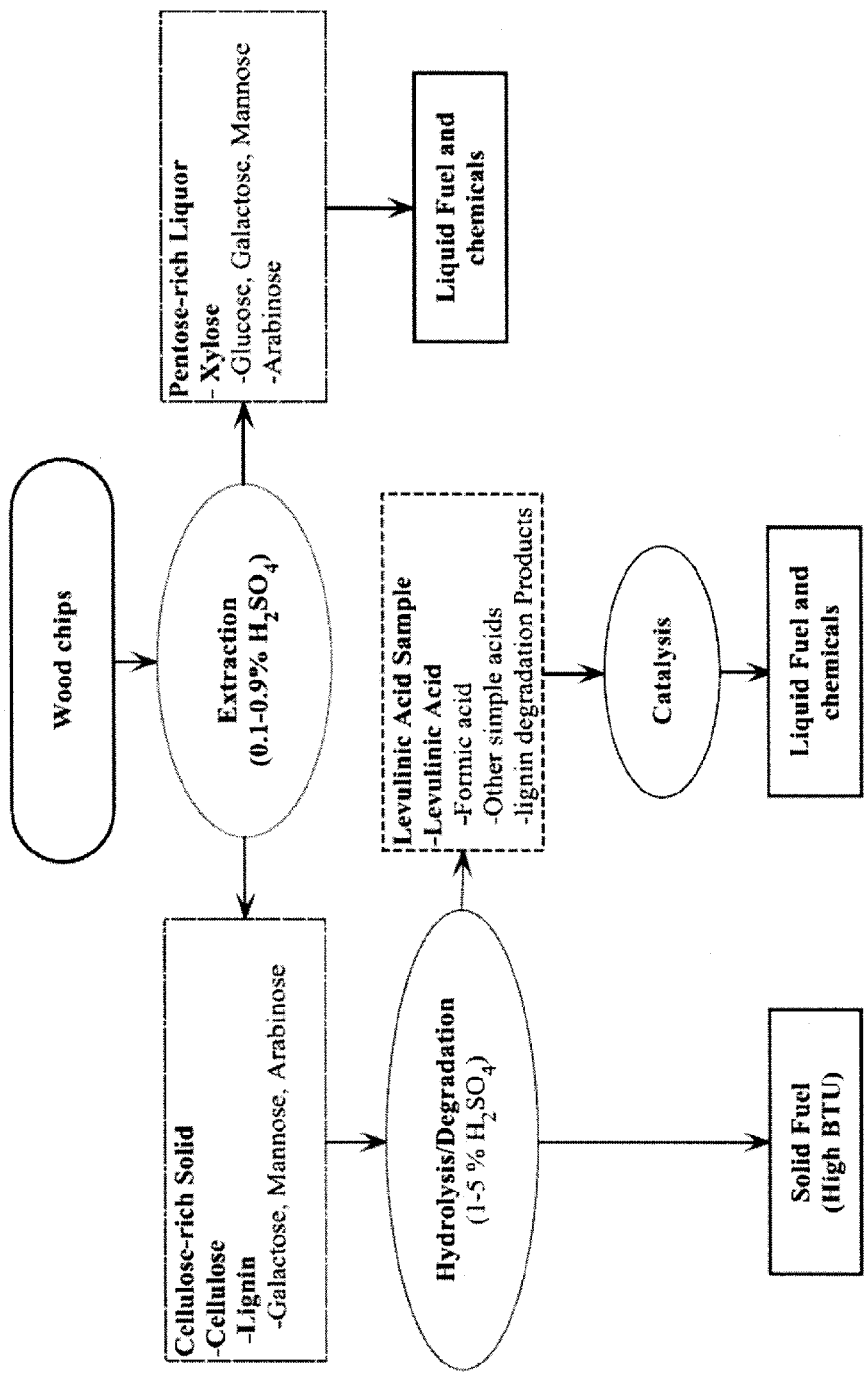
FIG. 2 is a simplified reaction scheme showing the conversion of carbohydrates from biomass (wood chips in this instance) into levulinic acid and other solid and/or liquid fuels and chemicals.

AA=acetic acid; F=furfural; FA=formic acid (FA); HMF=5-hydroxymethylfurfural; LA=levulinic acid; MTHF=methyltetrahydofuran; SA=sulfuric acid.

"Biomass" as used herein includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar or protein such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. "Biomass" includes virgin biomass and/or non-virgin biomass such as agricultural biomass, commercial organics, construction and demolition debris, municipal solid waste, waste paper, and yard waste. Municipal solid waste generally includes garbage, trash, rubbish, refuse and offal that is normally disposed of by the occupants of residential dwelling units and by business, industrial and commercial establishments, including but not limited to: paper and cardboard, plastics, food scraps, scrap wood, saw dust, and the like.

"Hexose" refers to a monosaccharide with six carbon atoms. Hexoses can be further characterized as aldohexoses (having an aldehyde functional group at position 1) or ketohexoses (having a ketone functional group at position 2 or 3). The word "hexose" encompasses all stereoisomers/anomers falling with the definition, as well as linear, hemiacetal, and/or hemiketal forms thereof. A "hexosan" is a polysaccharide that yields at least one hexose upon hydrolysis.

Lewis Acid/Base=A Lewis acid is defined herein as any chemical species that is an electron-pair acceptor, i.e., any chemical species that is capable of receiving an electron pair, without limitation. A Lewis base is defined herein as any chemical species that is an electron-pair donor, that is, any chemical species that is capable of donating an electron pair, without limitation.

In preferred versions of the invention, the Lewis acid (also referred to as the Lewis acid catalyst) may be any Lewis acid based on transition metals, lathanoid metals, and metals from Group 4, 5, 13, 14 and 15 of the periodic table of the elements, including boron, aluminum, gallium, indium, titanium, zirconium, tin, vanadium, arsenic, antimony, bismuth, lanthanum, dysprosium, and ytterbium. One skilled in the art will recognize that some elements are better suited in the practice of the method. Illustrative examples include $AlCl_3$, $(alkyl)AlCl_2$, $(C_2H_5)_2AlCl$, $(C_2H_5)_3Al_2Cl_3$, $BF_3$, $SnCl_4$ and $TiCl_4$.

The Group 4, 5 and 14 Lewis acids generally are designated by the formula $MX_4$; wherein M is Group 4, 5, or 14 metal, and X is a halogen independently selected from the group consisting of fluorine, chlorine, bromine, and iodine, preferably chlorine. X may also be a psuedohalogen. Non-limiting examples include titanium tetrachloride, titanium tetrabromide, vanadium tetrachloride, tin tetrachloride and zirconium tetrachloride. The Group 4, 5, or 14 Lewis acids may also contain more than one type of halogen. Non-limiting examples include titanium bromide trichloride, titanium dibromide dichloride, vanadium bromide trichloride, and tin chloride trifluoride.

Group 4, 5 and 14 Lewis acids useful in the method may also have the general formula $MR_nX_{4-n}$; wherein M is Group 4, 5, or 14 metal; wherein R is a monovalent hydrocarbon radical selected from the group consisting of $C_1$ to $C_{12}$ alkyl, aryl, arylalkyl, alkylaryl and cycloalkyl radicals; wherein n is an integer from 0 to 4; and wherein X is a halogen independently selected from the group consisting of fluorine, chlorine, bromine, and iodine, preferably chlorine. X may also be a psuedohalogen. Non-limiting examples include benzyltitanium trichloride, dibenzyltitanium dichloride, benzylzirconium trichloride, dibenzylzirconium dibromide, methyltitanium trichloride, dimethyltitanium difluoride, dimethyltin dichloride and phenylvanadium trichloride.

Group 4, 5 and 14 Lewis acids useful in method may also have the general formula $M(RO)_nR'_mX_{(m+n)}$; wherein M is Group 4, 5, or 14 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is an integer from 0 to 4; m is an integer from 0 to 4 such that the sum of n and m is not more than 4; and X is a halogen independently selected from the group consisting of fluorine, chlorine, bromine, and iodine, preferably chlorine. X may also be a psuedohalogen. Non-limiting examples include methoxytitanium trichloride, n-butoxytitanium trichloride, di(isopropoxy)titanium dichloride, phenoxytitanium tribromide, phenylmethoxyzirconium trifluoride, methyl methoxytitanium dichloride, methyl methoxytin dichloride and benzyl isopropoxyvanadium dichloride.

Group 5 Lewis acids may also have the general formula $MOX_3$; wherein M is a Group 5 metal; X is a halogen independently selected from the group consisting of fluorine, chlorine, bromine, and iodine, preferably chlorine. A non-limiting example is vanadium oxytrichloride.

The Group 13 Lewis acids have the general formula $MX_3$; wherein M is a Group 13 metal and X is a halogen independently selected from the group consisting of fluorine, chlorine, bromine, and iodine, preferably chlorine. X may also be a psuedohalogen. Non-limiting examples include aluminum trichloride, boron trifluoride, gallium trichloride, indium trifluoride, and the like.

The Group 13 Lewis acids useful in method may also have the general formula: $MR_nX_{3-n}$ wherein M is a Group 13 metal; R is a monovalent hydrocarbon radical selected from the group consisting of $C_1$ to $C_{12}$ alkyl, aryl, arylalkyl, alkylaryl and cycloalkyl radicals; and n is an number from 0 to 3; and X is a halogen independently selected from the group consisting of fluorine, chlorine, bromine, and iodine, preferably chlorine. X may also be a psuedohalogen. Non-limiting examples include ethylaluminum dichloride, methylaluminum dichloride, benzylaluminum dichloride, isobutylgallium dichloride, diethylaluminum chloride, dimethylaluminum chloride, ethylaluminum sesquichloride, methylaluminum sesquichloride, trimethylaluminum and triethylaluminum.

Group 13 Lewis acids useful in this disclosure may also have the general formula $M(RO)_nR'_mX_{3-(m+n)}$; wherein M is a Group 13 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3; m is an number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include methoxyaluminum dichloride, ethoxyaluminum dichloride, 2,6-di-tert-butylphenoxyaluminum dichloride, methoxy methylaluminum chloride, 2,6-di-tert-butylphenoxy methylaluminum chloride, isopropoxygallium dichloride and phenoxy methylindium fluoride.

Group 13 Lewis acids useful in this disclosure may also have the general formula $M(RC(O)O)_nR'_mX_{3-(m+n)}$; wherein M is a Group 13 metal; RC(O)O is a monovalent hydrocarbacyl radical selected from the group consisting of $C_2$ to $C_{30}$ alkacyloxy, arylacyloxy, arylalkylacyloxy, alkylarylacyloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3 and m is a number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include acetoxyaluminum dichloride, benzoyloxyaluminum dibromide, benzoyloxygallium difluoride, methyl acetoxyaluminum chloride, and isopropoyloxyindium trichloride.

The most preferred Lewis acids for use in the method are metal halides generally and more specifically transition metal halides, lathanoid metal halides, and Group 5, 13, and 14 metal halides. Preferred among the metal halides are metal chlorides. Preferred transition metal chlorides include, but are not limited to, $TiCl_4$, $VCl_3$, and the like. Preferred Group 13 and 14 metal halides and chlorides include, but are not limited to, $BF_3$, $AlCl_3$, $SnCl_4$, $InCl_3$, and $GaCl_3$. Preferred lanthanoid chlorides include, but are not limited to, $LaCl_3$, $DyCl_3$ and $YbCl_3$.

Mineral acid=any mineral-containing acid, including (by way of example and not limitation), hydrochloric acid, nitric acid, phosphoric acid, sulfuric acid, boric acid, hydrofluoric acid, hydrobromic acid, and the like. Organic acid=any organic acid, without limitation, such as toluensulfonic acid, formic acid, acetic acid, trifluoroacetic acid, oxalic acid, and the like.

Mono-, di- and trisaccharides=a monosaccharide is a carbohydrate having the general formula $C_x(H_2O)_y$, where x and y are integers from 3 to about 8. Monosaccharides are classified by the number of carbon atoms they contain: diose (2) triose (3) tetrose (4), pentose (5), hexose (6), heptose (7), etc. Disaccharides and trisaccharides are dimmers and trimers, respectively, of monosaccharides.

"Pentose" refers to a monosaccharide with five carbon atoms. Pentoses can be further characterized as aldopentoses (having an aldehyde functional group at position 1) or ketopentoses (having a ketone functional group at position 2 or 3). The word "pentose" encompasses all stereoisomers/anomers falling with the definition, as well as linear, hemiacetal, and hemiketal forms thereof. Aldopentoses include, for example, arabinose, lyxose, ribose, and xylose. Ketopentoses include, for example, ribulose and xylulose. A "pentosan" is a polysaccharide that yields at least one pentose upon hydrolysis.

A "solid acid catalyst" can comprise one or more solid acid materials. The solid acid catalyst can be used independently or alternatively can be utilized in combination with one or more mineral acid or other types of catalysts. Exemplary solid acid catalysts which can be utilized include, but are not limited to, heteropoly acids, acid resin-type catalysts, mesoporous silicas, acid clays, sulfated zirconia, molecular sieve materials, zeolites, and acidic material on a thermo-stable support. Where an acidic material is provided on a thermo-stable support, the thermo-stable support can include for example, one or more of silica, tin oxide, niobia, zirconia, titania, carbon, alpha-alumina, and the like. The oxides themselves (e.g., $ZrO_2$, $SnO_2$, $TiO_2$, etc.) which may optionally be doped with additional acid groups such as $SO_4$ may also be used as solid acid catalysts.

Further examples of solid acid catalysts include strongly acidic ion exchangers such as cross-linked polystyrene containing sulfonic acid groups. For example, the Amberlyst®-brand resins are functionalized styrene-divinylbenzene copolymers with different surface properties and porosities. The functional group is generally of the sulfonic acid type. The Amberlyst®-brand resins are supplied as gellular or macro-reticular spherical beads. (Amberlyst® is a registered trademark of the Dow Chemical Co.) Similarly, Nafion®-brand resins are sulfonated tetrafluoroethylene-based fluoropolymer-copolymers which are solid acid catalysts. Nafion® is a registered trademark of E.I. du Pont de Nemours & Co.)

Zeolites may also be used as solid acid catalysts. Of these, H-type zeolites are generally preferred, for example zeolites in the mordenite group or fine-pored zeolites such as zeolites X, Y and L, e.g., mordenite, erionite, chabazite, or faujasite. Also suitable are ultrastable zeolites in the faujasite group which have been dealuminated.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations shall include the corresponding plural characteristic or limitation, and vice-versa, unless otherwise specified or clearly implied to the contrary by the context in which the reference is made.

The processes described herein can be run in batch mode, semi-continuous mode, and/or continuous mode, all of which are explicitly included herein.

All combinations of method or process steps as used herein can be performed in any order, unless otherwise specified or clearly implied to the contrary by the context in which the referenced combination is made.

The methods described and claimed herein can comprise, consist of, or consist essentially of the essential elements and limitations of the disclosed methods, as well as any additional or optional ingredients, components, or limitations described herein or otherwise useful in synthetic organic chemistry.

EXAMPLES

The following examples are included solely to provide a more complete description of the process disclosed and claimed herein. The examples do not limit the scope of the claimed process in any fashion.

Materials & Methods:

Hybrid poplar, a fast growing, energy plantation crop, is among those plants that offer high-energy biomass and incredible improvements on greenhouse gas emissions. Moreover, hybrid poplar contains 14-18 wt % (based on wood weight) of pentosan which is mainly composed of xylan. Xylan decomposes to yield xylose, a pentose. Thus, hybrid poplar is a good carbohydrate source to test methods of separating pentoses prior to converting the hexoses to LA.[19] The NM-6 hybrid poplar, *Populus maximowiczii* x *nigra*, was specifically utilized for these examples. The NM-6 hybrid poplar is commercially available from a number of suppliers, including Cold Stream Farm (Freesoil, Mich.). The poplars used in these examples were 10 year-old trees harvested from northern Wisconsin and seasoned for three months prior to use. The poplar logs were hand debarked, chipped and screened, air dried, and cold stored.

The first stage of processing, a dilute acid extraction, was performed using a dual vessel pressurized reactor with heated liquor circulation. The extraction conditions were optimized to maximize the fractionation and extraction of pentosans from the hybrid poplar. The extraction conditions comprised treating the wood chips with an aqueous 1.0 wt % solution of sulfuric acid (~0.1 M, pH 1), at 160° C., for 60 min, at a liquor-to-wood ratio of 6. The slurry was centrifuged at 4000 rpm for 5 minutes to separate suspended materials. The supernatant was then further hydrolyzed with an aqueous 3 wt % solution of sulfuric acid, at 121° C., for 60 min. The supernatant so treated was then neutralized with a 0.6 M aqueous solution of NaOH, diluted with deionized water, and filtered through a 0.22 μm nylon filter.

The extraction conditions that maximized pentose hydrolysis/degradation (while simultaneously minimizing hexose hydrolysis/degradation) were scaled up to make enough solids for the second stage. The resultant solids were ground in a "WILEY"®-brand mill to pass a 3 mm screen. ("WILEY" is a registered trademark of Thomas Scientific, Swedesboro, N.J.) LA production from the extracted wood meal was performed using either a 2 L or 20 L "PARR"®-brand reactor. ("PARR" is a registered trademark of Parr Instrument Company, Moline, Ill.) Measured amounts of wood meal and $H_2SO_4$ were filled into temperature- and pressure-resistant glass tubes. The filled tubes were then placed into the "PARR"® reaction vessel. The reactions were controlled for the following variables: temperature, reaction time, sulfuric acid concentration, and substrate consistency (wood-to-liquor ratio). After each reaction was complete, the solids were washed out of the reactor and separated from the liquor via centrifugation at 4000 rpm for 10 min. The supernatant was neutralized, centrifuged, and filtered through 0.22 μm nylon filters.

Characterization of the supernatant for saccharides was performed using a "DIONEX"®-brand HPLC system (model ICS-3000) equipped with an integrated amperometric detector, a "CARBOPAC"®-brand PA20 guard column, and a "CARBOPAC"®-brand PA20 analytical column at 20° C. ("DIONEX" and "CARBOPAC" are registered trademarks of Dionex Corporation, Sunnyvale, Calif.) Eluent was provided at a rate of 0.6 mL/min, according to the following gradient: 0 to 20 min, 100% water; 20.1 to 30 min, 30% water and 70% 0.1 mol/L NaOH; 30.1 to 35 min, 100% water. 0.5 mol/L NaOH was used as post-column eluent. Simple organic acid and furans generated during extraction, such as acetic acid, formic acid, furfural, levulinic acid and 5-hydroxylmethylfurural (HMF) were analyzed using the Dionex ICS-3000 HPLC equipped with a Supelcogel™-brand C-610H column at temperature 50° C. and UV detector at 210 nm. ("Supelcogel" is an unregistered trademark of Sigma-Aldrich, St. Louis, Mo.) Eluent was 0.1% phosphoric acid at a constant rate of 0.7 mL/min.

Results & Discussion:

Biomass Characterization:

Samples from the hybrid poplar chips were analyzed for saccharides, lignin, and ash to characterize the material. Additionally, because the acidolysis used in the sugar analysis creates organic acid and furans, the major hydrolysis/degradation products of formic acid (FA) acetic acid (AA), levulinic acid (LA), 5-hydroxy-methyl-furfural (HMF), and furfural (F) were also characterized to provide a better reflection of the biomass composition. The results are shown in Table 1. The principal hemicellulose species present in this hybrid poplar is xylan, constituting about 15.0% of the dry weight.

TABLE 1

Characterization of Raw Material

| Arabinose | Galactose | Glucose | Xylose | Mannose | Saccharides |
|---|---|---|---|---|---|
| 0.30% | 0.50% | 40.70% | 13.30% | 3.00% | Total% |
| Formic | Acetic | LA[a] | HMF[a] | Furfural[b] | 57.80 |
| acid | acid | 0.60% | 0.70% | 1.80% | Degradation |
| 4.50% | 3.70% | Ash | AS Lignin | Klason | Products Total |
|  |  | 0.20% | 3.60% | 22.20% | 11.30% |
|  |  |  |  | Lignin | Lignin & Ash Total |
|  |  |  |  |  | 26.0% |
| Total Yield of Measured Components |  |  |  |  | 95.10% |

[a]Calculated on C6 sugars;
[b]Calculated on C5 sugars.

Extraction of Pentosans:

Following previous experimental work by the current inventors, mild sulfuric acid extraction conditions of 160° C., 60 min, 1.0 wt % $H_2SO_4$ and a 6:1 liquor-to-wood ratio were employed. These conditions liberated 85.0% of the pentosan content into the liquid fraction while only removing 8.0 wt % of hexosan content as shown in Table 2. The calculation considers both the directly measured sugar content and the degradations products which primarily occur during the additional hydrolysis during testing. This operation effectively fractionates the biomass into a pentose-rich liquid fraction and a hexose-rich solid that can be further processed into biofuels or materials.

TABLE 2

Characterization of the extracted biomass liquid fraction

| Arabinose | Galactose | Glucose | Xylose | Mannose | Pentoses |
|---|---|---|---|---|---|
| 0.34% | 0.38% | 1.74% | 9.22% | 1.26% | 9.56% |
| Hexoses | Formic acid | Acetic acid | LA[a] | HMF[a] | Furfural[b] |
| 3.38% | — | 2.83% | 0% | 0.16% | 1.99% |

[a]Calculated on C6 sugars;
[b]Calculated on C5 sugars.

LA Production from Extracted Solids:

The extracted hexose-rich chips were washed and ground in a "WILEY" mill to pass a 3 mm screen. The conditions were as follows: a temperature range of about 170 to 190° C., a sulfuric acid range of 1.0 to 5.0 wt %, a duration time range of from about 20 to 50 min, and a wood-to-liquor ratio range of 1:6 to 1:10 using the 2 liter "PARR" reactor. The wood meal, $H_2SO_4$ and water were filled into temperature- and pressure-resistant glass tubes inside the "PARR" reactor following a combined experimental design of Box-Behnken and CCF (central composite face), with four variables (temperature, acid concentration, ratio, duration time), was used to study the response pattern and to determine the optimum combination of variables. The statistical treatment combinations of the test variables along with the measured response values, expressed as levulinic acid yield corresponding to each combination are summarized in Table 3.

TABLE 3

Experimental design and results of LA production from extracted chips

| T (° C.) | $C_A$ (wt %) | L/W (Ratio) | t (min) | LA Yield (%)[a] |
|---|---|---|---|---|
| 170 | 1 | 6 | 20 | 7.12 |
| 170 | 5 | 6 | 20 | 26.94 |
| 170 | 1 | 10 | 20 | 10.08 |
| 170 | 5 | 10 | 20 | 37.35 |
| 170 | 3 | 8 | 20 | 18.52 |
| 170 | 3 | 8 | 35 | 18.08 |
| 170 | 5 | 8 | 35 | 32.74 |
| 170 | 1 | 8 | 35 | 9.49 |
| 170 | 3 | 6 | 35 | 19.35 |
| 170 | 3 | 10 | 35 | 25.74 |
| 170 | 1 | 6 | 50 | 7.93 |
| 170 | 5 | 6 | 50 | 28.33 |
| 170 | 1 | 10 | 50 | 14.96 |
| 170 | 5 | 10 | 50 | 47.75 |
| 170 | 3 | 8 | 50 | 23.79 |
| 180 | 3 | 8 | 20 | 26.96 |
| 180 | 1 | 8 | 20 | 14.93 |
| 180 | 3 | 10 | 20 | 33.38 |
| 180 | 5 | 8 | 20 | 39.50 |
| 180 | 3 | 6 | 20 | 20.52 |
| 180 | 1 | 8 | 35 | 19.47 |
| 180 | 5 | 8 | 35 | 41.16 |
| 180 | 3 | 6 | 35 | 25.94 |
| 180 | 3 | 10 | 35 | 33.38 |
| 180 | 3 | 8 | 35 | 36.43 |
| 180 | 5 | 6 | 35 | 37.01 |
| 180 | 5 | 10 | 35 | 51.04 |
| 180 | 1 | 6 | 35 | 11.71 |
| 180 | 1 | 10 | 35 | 15.10 |
| 180 | 3 | 8 | 50 | 31.57 |
| 180 | 1 | 8 | 50 | 25.89 |
| 180 | 3 | 6 | 50 | 29.42 |
| 180 | 5 | 8 | 50 | 44.80 |
| 180 | 3 | 10 | 50 | 47.85 |
| 190 | 1 | 6 | 20 | 25.91 |
| 190 | 5 | 6 | 20 | 41.01 |
| 190 | 1 | 10 | 20 | 32.06 |
| 190 | 5 | 10 | 20 | 50.41 |
| 190 | 3 | 8 | 20 | 35.60 |
| 190 | 3 | 8 | 35 | 35.70 |
| 190 | 1 | 8 | 35 | 40.97 |
| 190 | 3 | 6 | 35 | 35.87 |
| 190 | 3 | 10 | 35 | 52.29 |
| 190 | 5 | 8 | 35 | 52.87 |
| 190 | 1 | 6 | 50 | 25.55 |
| 190 | 5 | 6 | 50 | 46.72 |
| 190 | 1 | 10 | 50 | 38.43 |
| 190 | 5 | 10 | 50 | 54.09 |
| 190 | 3 | 8 | 50 | 39.87 |

[a]LA yield was calculated as percent of theoretical based on the initial biomass hexose content.

The yield calculated is a theoretical yield based on the initial biomass hexose content. This yield considers the experiments' hybrid poplar chips hexose content, which was 45.1 wt % and the mass loss of 64.5 wt % of converting levulinic acid from hexose due to the dehydration. 18 Therefore a 100% yield is equivalent to a 29.1 wt % on an initial biomass basis.

Data analysis on the yield data was done using the DOE (Design of Experiments) software MODDE 7.0 by Umetrics AB (Malmo, Sweden; a wholly owned subsidiary of MKS Instruments, Andover, Mass.), and the statistical model fitting results are shown in Table 4.

TABLE 4

Significance or regression coefficient for LA yield

| | Coefficient | Std. Error | Significance Level P value |
|---|---|---|---|
| Constant | 31.3621 | 0.522217 | 0 |
| Temp | 7.13644 | 0.527312 | 2.74773e−017 |
| Ca | 8.49118 | 0.527312 | 4.62373e−020 |
| t | 2.21523 | 0.527312 | 0.000127642 |
| R | 3.95099 | 0.527312 | 2.18191e−009 |
| Temp * Ca | −1.21615 | 0.495324 | 0.0181 |
| Ca * R | 0.829409 | 0.495324 | 0.10113 |
| t * R | 0.686719 | 0.495323 | 0.172608 |

N = 52,
$Q^2$ = 0.817,
Degree of Freedom = 44,
$R^2$ = 0.923,
Y-miss = 0
$R^2$ Adj. = 0.911,
RSD = 3.7658,
Confidence level = 0.95

Partial Least Squares (PLS) was used to estimate the coefficients of the terms in the model. Usually, a P value less than 0.0500 indicates the model term is significant, while a P value greater than 0.1000 indicates the model term is not significant. From Table 4, it can be seen that the first order main effects of four variables were highly significant as was evident from their P values. This suggested that the four variables were directly related to the production of levulinic acid. The second order main effects of temperature and acid concentration were also significant, with the P value being 0.0181.

The predictive power of a PLS model is given by $Q^2$, which is based on the Prediction Residual Sum of Squares, PRESS. This is a measure of how well the model will predict the responses for new experimental condition. A $Q^2$ larger than zero indicates that the variable is significantly predictive. A $Q^2$ value of 0.7 or larger indicates that the model has good predictive ability and will have small prediction errors. $Q^2$ is the predictive measure corresponding to the measure of fit, whereas $R^2$ is the percent variation of the response explained by the model. $Q^2$ gives a lower estimate to how well the model predicts the outcome of new experiments, while $R^2$ gives an upper estimate. $Q^2$ and $R^2$ of the model described herein were 0.82 and 0.92, respectively, which indicates that the model has good predictive ability and there is a good fit between the experimental concentration of levulinic acid and the kinetic model for a broad range of reaction conditions.

Figure 3:
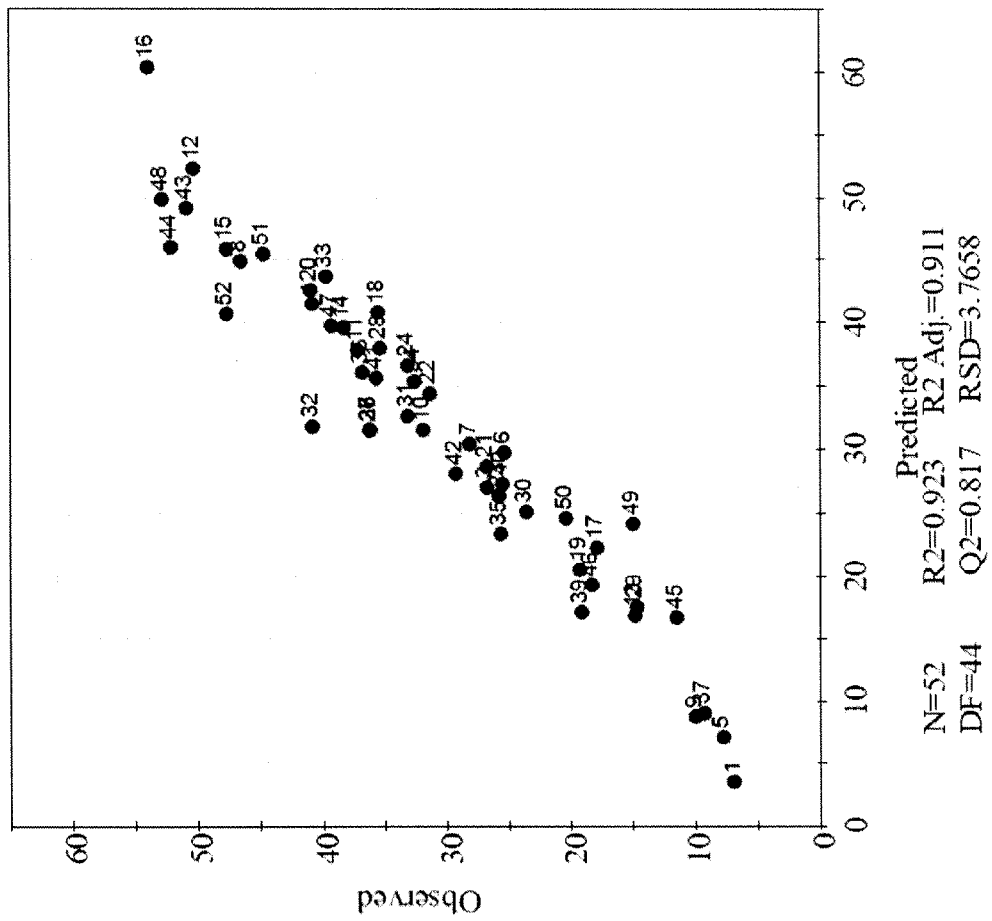
FIG. 3 is a parity plot depicting the experimental versus modeled yield of levulinic acid using the method described herein.

The model fitting yielded the following regression equation, which was an empirical relationship between levulinic acid yield and the variable, shown in equation 1. The predicted yield was plotted against the measured yield in a Parity Plot in FIG. 3. The regression equation's goodness of fit was shown to be quite high with a linear fit, no outliers, and a $R^2$ statistic of 0.923.

$$Y_{LA}(t\%) = 31.36 + 7.14T + 8.49C_A + 2.22t - 3.98R - 1.22TC_A + 0.83C_AR + 0.69Rt \quad \text{Equation 1:}$$

Using the optimizer of the MODDE software, a predicted 60.3% of the theoretic yield could be obtained under the conditions of 190° C., 50 min, 5% wt $H_2SO_4$ and a wood-to-liquor ratio of 10. This is quite promising as it in range or higher than other reported processes (45.6~68.8%)[20-22] and produces a pentose stream that can be utilized to create other products to provide value.

LA Production from Non-Extracted Solids:

Utilizing the optimized conditions, replicates were prepared to validate the model and determine the repeatability of the predicted yields. Additionally, it was desired to see the impact of extraction on yield of LA. Thus control experiments of non-extracted biomass were also included. Utilizing the optimized conditions, replicate experiments were performed on three replicates of non-extracted biomass at a 2 L scale, two replicates of extracted biomass at a 2 L scale, and three replicates of extracted biomass at a 20 L scale.

Figure 4:
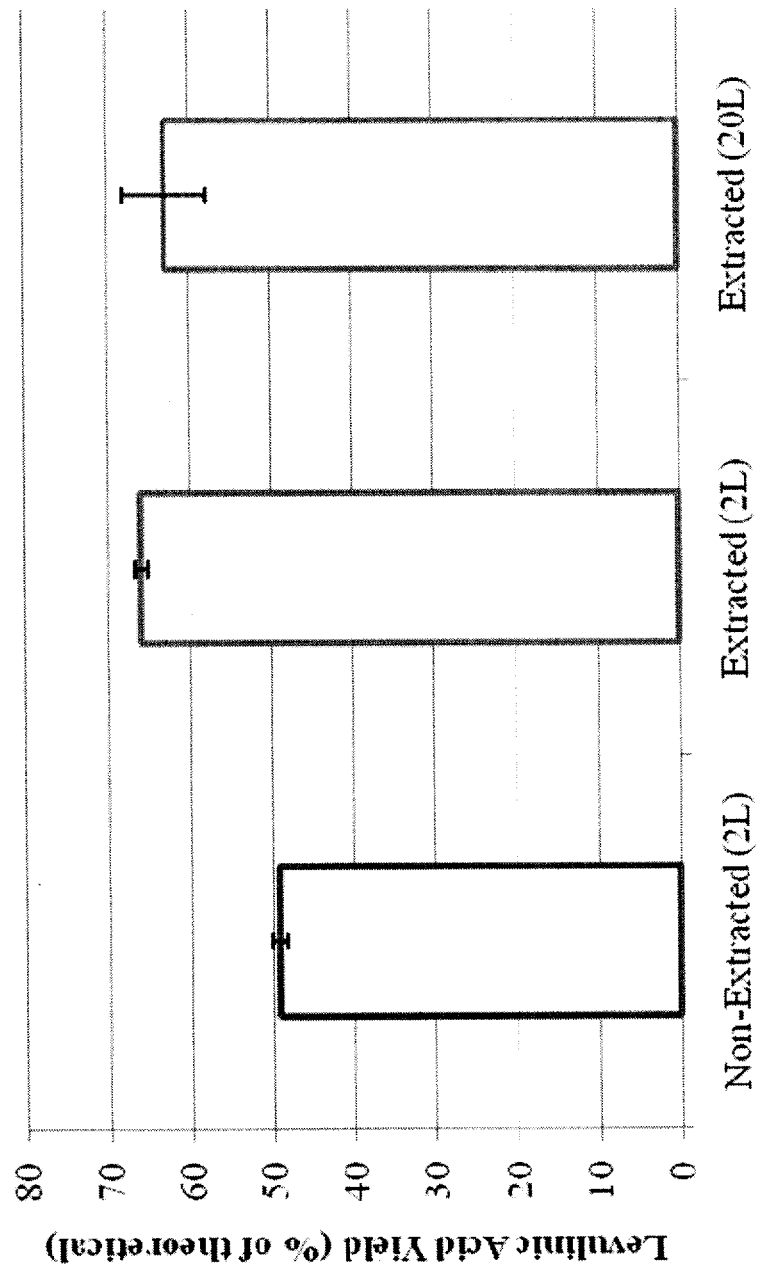
FIG. 4 is a histogram showing actual yield of levulinic acid (as a percentage of theoretical yield) for the method described herein (p>95) using non-extracted biomass (2 L volume), extracted biomass (2 L volume), and extracted biomass (20 L volume).

The resulting formed LA was measured, % of theoretical yield calculated, and plotted in FIG. 4. As shown in FIG. 4, the extracted biomass has a significantly higher LA yield than the non-extracted biomass. These yields are on the same basis and include the minor losses of hexoses that occur in the extraction step.

The examples show that a two-stage acid-catalytic conversion of carbohydrates into levulinic acid provides a higher actual yield of LA than a single-stage process. Conditions were utilized to extract 85.0 wt % of pentosan from the biomass reactant, with more than 92.0 wt % of hexosan retained in the solids for LA production. The pentose-extracted solids were subjected to a range of harsh acid conditions, and the yield of LA production from the extracted solids was modeled as a function of temperature, acid concentration, duration time and wood-to-liquor ratio. The LA yield model was shown to have good predictive ability and fit between the experimental concentration of levulinic acid and the kinetic model for a broad range of reaction conditions. Results showed that the yield of LA was favored at high acid concentration, high temperature and high liquor-to-wood ratio. A maximum LA yield of 17.8 wt % on a original biomass basis was predicted, which represented a theoretic yield of 60.3% was obtained under conditions of 190° C., 50 min, sulfuric acid concentration 5 wt %, and liquor-to-wood ratio of 10:1. The model results were validated utilized several replicates and different reactors. The highest yield was obtained from the reactor with the best heat transfer and mixing which suggests additional yield increases are possible.

REFERENCES (1) Bozell, J., Production of levulinic acid and use as a platform chemical for derived products. *Resources, Conservation and Recycling* 2000, 28, (3-4), 227-239.

(2) Farnleitner, L.; Stueckler, H.; Kaiser, H.; Kloimstein, E. Preparation of stable levulinic acid. 3920340, 1991.

(3) Itaya, H.; Shiotani, A.; Toriyahara, Y. Preparation of levulinic acid from furfuryl alcohol. 62252742 1998.

(4) Edwards III, W. Preparation of oxycarboxylic acids. 4612391, 1986.

(5) Lourvanij, K.; Rorrer, G., Dehydration of glucose to organic acids in microporous pillared clay catalysts. *Applied Catalysis A: General* 1994, 109, (1), 147-165.

(6) Hayes, D. J.; Ross, P. J.; Hayes, P. M. H. B.; Fitzpatrick, P. S., The Biofine Process: Production of Levulinic Acid, Furfural and Formic Acid from Lignocellulosic Feedstocks. In 1999.

(7) Girisuta, B.; Janssen, L. P. B. M.; Heeres, H. J., Green Chemicals: A Kinetic Study on the Conversion of Glucose to Levulinic Acid. *Chemical Engineering Research and Design* 2006, 84, (5), 339-349.

(8) Girisuta, B.; Janssen, L. P. B. M.; Heeres, H. J., Kinetic Study on the Acid-Catalyzed Hydrolysis of Cellulose to Levulinic Acid. *Industrial & Engineering Chemistry Research* 2007, 46, (6), 1696-1708.

(9) Tarabanko, V.; Chernyak, M.; Aralova, S.; Kuznetsov, B., Kinetics of levulinic acid formation from carbohydrates at moderate temperatures. *Reaction Kinetics and Catalysis Letters* 2002, 75, (1), 117-126.

(10) Efremov, A. A.; Pervyshina, G. G.; Kuznetsov, B. N., Production of levulinic acid from wood raw material in the presence of sulfuric acid and its salts. *Chemistry of Natural Compounds* 1998, 34, (2), 182-185.

(11) Fitzpatrick, S., Production of levulinic acid by the hydrolysis of carbohydrate-containing materials. *World Patent* 1997, 9640609.

(12) Mosier, N.; Ladisch, C.; Ladisch, M., Characterization of acid catalytic domains for cellulose hydrolysis and glucose degradation. *Biotechnology and bioengineering* 2002, 79, (6), 610-618.

(13) Montané, D., High-temperature dilute-acid hydrolysis of olive stones for furfural production. *Biomass and Bioenergy* 2002, 22, (4), 295-304.

(14) Antal, M. J.; Leesomboon, T.; Mok, W. S.; Richards, G. N., Mechanism of formation of 2-furaldehyde from D-xylose. *Carbohydrate Research* 1991, 217, 71-85.

(15) Lima, S.; Pillinger, M.; Valente, A., Dehydration of d-xylose into furfural catalysed by solid acids derived from the layered zeolite Nu-6(1). *Catalysis Communications* 2008, 9, (11-12), 2144-2148.

(16) Dias, A. S.; Pillinger, M.; Valente, A. A., Dehydration of xylose into furfural over micro-mesoporous sulfonic acid catalysts. *Journal of Catalysis* 2005, 229, (2), 414-423.

(17) Dias, A. S.; Lima, S.; Carriazo, D.; Rives, V.; Pillinger, M.; Valente, A. A., Exfoliated titanate, niobate and titanoniobate nanosheets as solid acid catalysts for the liquid-phase dehydration of D-xylose into furfural. *Journal of Catalysis* 2006, 244, (2), 230-237.

(18) Leonard, R., Levulinic acid as a basic chemical raw material. *Industrial & Engineering Chemistry* 1956, 48, (8), 1330-1341.

(19) Wiselogel, A.; Tyson, S.; Johnson, D., Biomass feedstock resources and composition. In *Handbook on bioethanol: Production and utilization,* 1996; pp 105-118.

(20) Chang, C.; Cen, P.; Ma, X., Levulinic acid production from wheat straw. *Bioresource technology* 2007, 98, (7), 1448-1453.

(21) Fang, Q.; Hanna, M. A., Experimental studies for levulinic acid production from whole kernel grain *sorghum*. *Bioresource technology* 2002, 81, (3), 187-192.

(22) Cha, J.; Hanna, M., Levulinic acid production based on extrusion and pressurized batch reaction. *Industrial Crops and Products* 2002, 16, (2), 109-118.

What is claimed is:

1. A method of producing levulinic acid from biomass, the method comprising:
   (a) treating biomass with a first aqueous acidic solution at a pH, for a time, and temperature such that at least a portion of pentosans contained within the biomass is extracted from the biomass, to yield pentosan-extracted biomass; and
   (b) treating the pentosan-extracted biomass with a second aqueous acidic solution at a pH, for a time, and a temperature, such that at least a portion of hexosans contained within the pentosan-extracted biomass are converted to levulinic acid.

2. The method of claim 1, wherein step (a) comprises treating the biomass with an aqueous acidic solution having a pH of from about 0.8 to about 1.5, for about 5 minutes to about 5 hours, at a temperature from about 100° C. to 300° C.

3. The method of claim 1, wherein step (a) comprises treating the biomass with an aqueous acidic solution having a pH of from about 0.9 to about 1.2, for about 10 minutes to about 3 hours, at a temperature from about 125° C. to 200° C.

4. The method of claim 1, wherein step (a) comprises treating the biomass with an aqueous acidic solution having a pH of from about 0.8 to about 1.0, for about 10 minutes to about 1 hour, at a temperature from about 125° C. to 175° C.

5. The method of any one of claims 1 to 4, wherein step (b) comprises treating the biomass with an aqueous acidic solution having a pH of from about 0.2 to about 0.6, for about 5 minutes to about 5 hours, at a temperature from about 100° C. to 300° C.

6. The method of any one of claims 1 to 4, wherein step (b) comprises treating the biomass with an aqueous acidic solution having a pH of from about 0.2 to about 0.6, for about 10 minutes to about 3 hours, at a temperature from about 150° C. to 250° C.

7. The method of any one of claims 1 to 4, wherein step (b) comprises treating the biomass with an aqueous acidic solution having a pH of from about 0.2 to about 0.6, for about 10 minutes to about 1 hour, at a temperature from about 170° C. to 190° C.

8. The method of claim 1, wherein in step (a) and in step (b), the aqueous acidic solution independently comprises a mineral acid or a Lewis acid.

9. The method of claim 8, wherein the mineral acid is selected from the group consisting of hydrochloric acid, nitric acid, phosphoric acid, sulfuric acid, boric acid, hydrofluoric acid, and hydrobromic acid.

10. The method of claim 9, wherein the mineral acid is sulfuric acid.

11. The method of claim 1, further comprising, after step (a) and before step (b), separating the first aqueous acidic solution from the pentosan-extracted biomass, and further comprising converting pentosans contained in the first aqueous acidic solution into furfural.

12. The method of claim 11, wherein step (a) comprises treating the biomass with an aqueous acidic solution having a pH of from about 0.8 to about 1.5, for about 5 minutes to about 5 hours, at a temperature from about 100° C. to 300° C.

13. The method of claim 11, wherein step (a) comprises treating the biomass with an aqueous acidic solution having a pH of from about 0.9 to about 1.2, for about 10 minutes to about 3 hours, at a temperature from about 125° C. to 200° C.

14. The method of claim 11, wherein step (a) comprises treating the biomass with an aqueous acidic solution having a pH of from about 0.8 to about 1.0, for about 10 minutes to about 1 hour, at a temperature from about 125° C. to 175° C.

15. The method of claim 11, wherein step (b) comprises treating the biomass with an aqueous acidic solution having a pH of from about 0.2 to about 0.6, for about 5 minutes to about 5 hours, at a temperature from about 100° C. to 300° C.

16. The method of claim 11, wherein step (b) comprises treating the biomass with an aqueous acidic solution having a pH of from about 0.2 to about 0.6, for about 10 minutes to about 3 hours, at a temperature from about 150° C. to 250° C.

17. The method of claim 11, wherein step (b) comprises treating the biomass with an aqueous acidic solution having a pH of from about 0.2 to about 0.6, for about 10 minutes to about 1 hour, at a temperature from about 170° C. to 190° C.

18. The method of claim 11, wherein in step (a) and in step (b), the aqueous acidic solution independently comprises a mineral acid or a Lewis acid.

19. The method of claim 18, wherein the mineral acid is selected from the group consisting of hydrochloric acid, nitric acid, phosphoric acid, sulfuric acid, boric acid, hydrofluoric acid, and hydrobromic acid.

* * * * *